US008617130B2

(12) United States Patent
Ray (10) Patent No.: US 8,617,130 B2
(45) Date of Patent: Dec. 31, 2013

(54) INSULATED DISPOSABLE SURGICAL FLUID CONTAINER

(76) Inventor: Stephen P. Ray, Trevor, WI (US)

( * ) Notice: Subject to any disclaimer, the term of this patent is extended or adjusted under 35 U.S.C. 154(b) by 0 days.

(21) Appl. No.: 13/453,340

(22) Filed: Apr. 23, 2012

(65) Prior Publication Data

US 2013/0281961 A1    Oct. 24, 2013

(51) Int. Cl.
*A61M 1/00*    (2006.01)
(52) U.S. Cl.
USPC .......................................... 604/317; 604/403
(58) Field of Classification Search
USPC .................. 604/289–310, 317–327, 403–410
See application file for complete search history.

(56) References Cited

U.S. PATENT DOCUMENTS

| 4,068,034 A | * | 1/1978 | Segawa et al. ................ 428/421 |
| 4,392,594 A | * | 7/1983 | Swett et al. ................... 222/530 |
| 4,795,435 A | | 1/1989 | Steer |
| 4,947,896 A | | 8/1990 | Bartlett |
| 5,045,076 A | * | 9/1991 | Pierce ........................... 604/317 |
| 5,618,278 A | | 4/1997 | Rothrum |
| 5,915,628 A | * | 6/1999 | Kreizel .......................... 239/377 |
| 6,155,620 A | | 12/2000 | Armstrong |
| 7,195,617 B2 | | 3/2007 | Papendick et al. |
| 7,306,120 B2 | * | 12/2007 | Hughes .......................... 222/158 |
| 8,382,730 B2 | | 2/2013 | Tauer |
| 2009/0159607 A1 | * | 6/2009 | Kratzer ......................... 220/849 |
| 2012/0143241 A1 | | 6/2012 | Ray |

FOREIGN PATENT DOCUMENTS

WO PCT/US2013/037714    4/2013

* cited by examiner

*Primary Examiner* — Philip R Wiest
*Assistant Examiner* — Benjamin Klein
(74) *Attorney, Agent, or Firm* — Lesavich High-Tech Law Group, P.C.; Stephen Lesavich (57) ABSTRACT

An insulated disposable surgical fluid container. The container is doubled walled and includes an outer surface including an insulating material for reducing heat transfer from the outer surface to a surrounding area an insulating component separating the outer surface from an inner surface for reducing heat transfer from the inner surface to the outer surface and an inner surface comprising a fluid container portion for holding a fluid. The inner surface includes a thermally conductive material for spreading heat energy evenly over the inner surface and maintaining an isothermal temperature distribution on the inner surface, thereby maintaining an isothermal temperature of any fluid included in the fluid container portion. The fluid container portion includes a keel shaped bottom portion for accurately dispensing and pouring irrigating fluids from the fluid container portion into a wound during a surgery. The container helps prevent perioperative hypothermia from irrigations fluids used during a surgery.

15 Claims, 6 Drawing Sheets

SIDE VIEW - CLOSED

FIG. 1

SIDE VIEW - CLOSED

FIG. 2
SIDE VIEW - OPEN

FIG. 3

TOP VIEW - CLOSED

FIG. 4

SIDE VIEW - CLOSED

FIG. 5
FRONT VIEW - CLOSED

FIG. 6

PRIOR ART
FORCES ON A BOAT
KEEL

INSULATED DISPOSABLE SURGICAL FLUID CONTAINER

FIELD OF THE INVENTION

This invention relates to surgical instruments. More specifically, it relates to an insulated disposable surgical fluid container.

BACKGROUND OF THE INVENTION

It is common practice to use irrigation fluids (e.g., 0.9% or other concentration sodium chloride, lactated Ringer's solutions, etc.) to wash out debris, blood, tissue, fat or unwanted body fluids during surgeries on human. Antibiotic irrigation fluids are also used during surgery to prevent infection.

Such irrigation fluids are sold in flexible packages and semi-rigid and rigid glass and plastic bottles. However, such irrigation fluids may cause problems if they are not maintained at a proper temperature.

"Thermoregulation" is a human body's way to maintain homeostasis by keeping body temperature between certain boundaries regardless of temperatures in the external environment. "Normothermia" for a human body includes a core temperature in the range of about 36° C. to 38° C. (96.8° F. to 100.4° F.). "Hypothermia" for a human body includes a core temperature less than about 36° C. (96.8° F.).

Inadvertent "perioperative hypothermia" is a common but preventable complication of surgical procedures. Surgical patients are at risk of developing hypothermia at any stage of the perioperative pathway.

If the human body is unable to maintain a certain temperature, due to external stressors such as anesthesia, or use of cold Intravenous (IV) and irrigation fluids during a surgery, "homeostatic imbalance" occurs. It has been widely recognized and reported that "perioperative hypothermia" is a contributing factor in the development of surgical site infections, also contributing to longer length of hospital stay and an increased risk for mortality during and after surgery.

There is abundant research showing increased patient risks intra and post operatively associated with a drop in core body temperature during the surgical procedure. Heat loss occurs through different mechanisms including conduction loss, convection loss and radiated heat loss. Open wounds present a challenge because large surface areas with abundant blood supply speed up the heat loss to an environment cooler than body temperature.

One study published in the journal Anesthesiology revealed that less than one degree of hypothermia is enough to "significantly increase blood loss during surgery," while other published studies indicate that a similar degree of hypothermia is also enough to significantly increase the need for blood transfusions.

Virtually any patient regardless of age, race, gender, health and fitness status, and length or type of procedure is at risk for surgery-related hypothermia. The reason being is hypothermia is a body's normal reaction to the induction of anesthesia. When anesthesia is administered, or cool/cold IV and irrigation fluids are used, core-to-peripheral redistribution of body heat occurs, which lowers overall body temperature. Post anesthetic shivering is also one of the leading causes of discomfort for patients recovering from general anesthesia. The causes of shivering primarily include hypothermia from thermoregulation inhibition by anesthetics.

Irrigation fluids used to irrigate/wash a body cavity during a surgery include moderate (500 mls to 1000 mls) to volumes large volumes including those greater than 2000 mls, are routinely used.

Using cool or cold IV or irrigation fluids in a patient during a surgery further aggravates perioperative hypothermia symptoms.

The, temperatures in operating rooms are typically set in the range of 60° F. (16° C.) to 70° F. (21° C.), which is cold compared to normal body temperatures of 98.6° F. IV and irrigation fluids are often placed in basins or other single walled containers without covers in an operating room during a surgery. The fluids are often cooled very quickly to way below normal body temperature (98.6° F., 37° C.) because most operating rooms include cooling air flows (e.g., air conditioning, etc.).

Irrigating solutions are kept in warming units at about 108° F. (37° C.). The solution is. poured into an open top basin or single walled containers and is kept on aback table that holds the surgical instruments. When the solution is needed it is poured into the wound from the container or flushed using a bulb syringe. Most of the time the solution sitting in the open container loses heat and often approaches the ambient room temperature of the operating room, which is about 60° F. (16° C.) to 70° F. (21° C.).

The irrigating solutions in basins or single walled containers very often distinctly cold to the touch. The solution becomes a heat sink that robs the body of heat making it more difficult to maintain a normal body temperature during a surgery further aggravates perioperative hypothermia symptoms. The longer the surgical procedure and the larger the wound the greater the potential heat loss.

One of the most common interventions used to prevent perioperative hypothermia is warming IV and irrigation solutions. Fluids for irrigation may be warmed in devices up to 110° F., (43° C.).

One study has shown that patients with warmed IV and irrigation fluids demonstrated a higher core body temperature than the non-warmed: 36.8° C. (98.2° F.) versus 35.5° C. (95.9° F.). Another study has shown that irrigation with lactated Ringer's solution warmed up to 39° C. did not show any incidences of hypothermia.

There are many types of fluid warmers know in the art. They include warming basins, warming towers, warming pots, etc. in which an irrigation solution is physically placed and warming cabinets.

For example, one irrigation solution warmer includes a heated basin in which irrigation solution is placed. The device maintains irrigation solution temperatures of solution that is poured back into a table basin. However, the warmer is another device that must be purchased, maintained and its basin autoclaved and/or sterilized and requires another electrical outlet in the operating room during surgery. In addition the basin is awkward to pour irrigation solution from or extract it with an irrigation bulb syringe. Warming towers and warming pots have similar problems.

Another irrigation solution warmer includes a warming cabinet. To warm irrigation solutions, a dry warming cabinet with carefully controlled temperatures is used. The warming cabinet will be controlled by a calibrated thermometer. However, the warmer is another device that must be purchased and maintained and requires another electrical outlet in the operating room during surgery.

In addition, another problem is that during a warming period in a warming cabinet, overwrap packaging and/or pour bottles are left intact on flexible intravenous and irrigation containers to ensure sterile solution integrity. Once removed from the warming cabinet, solutions must be used within 24 hours and/or discarded, and not returned to stock supply or re-warmed. This often leads to waste of irrigation solutions.

Another problem is when a warming cabinet is used, the irrigation fluids are typically transferred to an open metal or plastic fluid basin or single walled container without a top, which is used to pour the irrigation fluids directly into a wound and/or used to extract fluids with an irrigation bulb syringe. The basin are hard to pour.

Another problem is that all types of irrigation solution warmers must have an operational check, cleaning and preventive maintenance inspection at least semiannually to ensure patient safety. The inspection includes electrical and temperature safety.

Another problem is that even if irrigation fluids are warmed by warming devices or in a warming cabinet, they cool off very rapidly in a cool operating room. Thus, even when a warming device/cabinet is used, perioperative hypothermia can occur if the fluids sit for too long a time period in the basins. A circulating surgical nurse typically has to make multiple trips to a fluid warmer (usually in an adjacent room) to keep getting irrigating solutions that are warm.

Thus, it is desirable to solve some of the many problems associated with warming irrigation fluids used for surgery on humans and help prevent perioperative hypothermia.

SUMMARY OF THE INVENTION

In accordance with preferred embodiments of the present invention, some of the problems associated with fluids used during a surgery overcome. An insulated disposable surgical fluid container is presented.

The container is doubled walled and includes an outer surface including an insulating material for reducing heat transfer from the outer surface to a surrounding area an insulating component separating the outer surface from an inner surface for reducing heat transfer from the inner surface to the outer surface, the inner surface comprising a fluid container portion for holding a fluid. The inner surface includes a thermally conductive material for spreading heat energy evenly over the inner surface and maintaining an isothermal temperature distribution on the inner surface, thereby maintaining an isothermal temperature of any fluid included in the fluid container portion. The fluid container portion includes a keel shaped bottom portion for accurately dispending and pouring irrigating fluids from the fluid container portion into a wound during a surgery.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein.

DETAILED DESCRIPTION OF THE INVENTION

Figure 1:
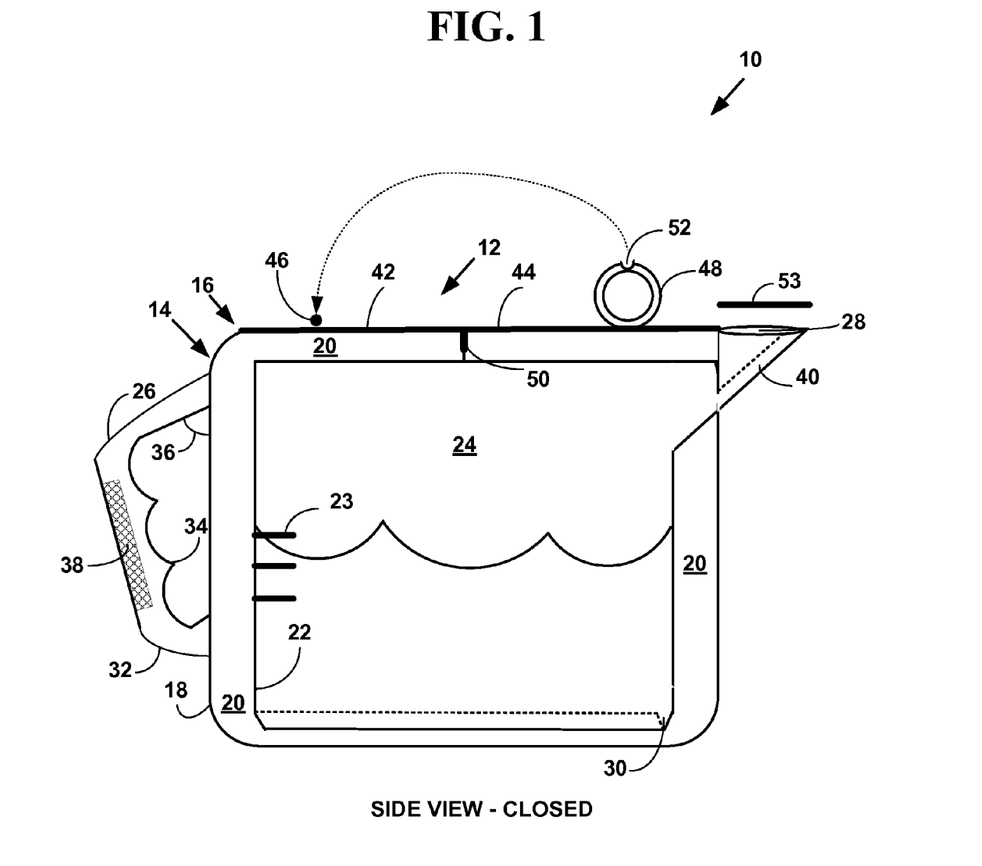
FIG. 1 is a block diagram illustrating a side view of an insulated disposable surgical fluid container apparatus with a closed cover.

FIG. 1 is a block diagram illustrating a side view of an insulated disposable surgical fluid container apparatus 12 with a closed cover. The apparatus 12 includes a triangular shaped bottom portion 14 and a triangular shaped top portion 16.

The triangular shaped bottom portion 14 includes an outer surface 18, an insulating component 20 between the outer surface and an inner surface 22 separating the outer surface from the inner surface by a pre-determined distance, a fluid container portion 24 in the inner surface, an ergonomic handle portion 26, and a pouring portion 28. The outer surface 18 and inner surface 20 form a double-wall container.

The outer surface 18 includes an insulating material for reducing heat transfer from the outer surface to a surrounding area. The insulating material of the outer surface 18 prevents irrigation fluids in the fluid container portion 24 from losing heat and being affected by cooler temperatures in an operating room.

Conventional plastics (e.g., PEI, PVC, etc.) are considered thermal insulators. Thermal insulators prevent heat loss.

In one embodiment, outer surface 18 is created from Polyetherimide, Polyimide other thermosetting polyimides, other plastics and/or composite materials.

In another embodiment, the outer surface is created from Polyvinyl chloride (PVC) polyethylene and/or polypropylene.

However, the present invention is not limited to these materials and other materials can be used for the outer surface 18 to practice the invention.

"Polyetherimide" (PEI) is an amorphous, amber-to-transparent thermoplastic with characteristics similar to the related plastic PEEK. Polyether ether ketone (PEEK) is a colorless organic polymer thermoplastic Relative to PEEK, PEI is cheaper, but less temperature-resistant and lower in impact strength.

For example, commercially, ULTEM is a family of PEI products manufactured by SABIC. ULTEM resins are used in medical and chemical instrumentation due to their heat resistance, solvent resistance and flame resistance.

"Polyimide" (PI) is a polymer of imide monomers. Such imide monomers include pyromellitic dianhydride and 4,4'-oxydianiline and others. Polyimide materials are lightweight, flexible, resistant to heat and chemicals. Polyimide parts are not affected by commonly used solvents and oils, including hydrocarbons, esters, ethers, alcohols and freons. They also resist weak acids.

"Thermosetting polyimides" are known for thermal stability, good chemical resistance, excellent mechanical properties. Normal operating temperatures for such polymides range from cryogenic with temperatures below about −238° F. (−150° C.) to those exceeding about 500° F. (260° C.).

"Composite materials" are engineered or naturally occurring materials made from two or more constituent materials with significantly different physical or chemical properties which remain separate and distinct at the macroscopic or microscopic scale within the finished structure. Common polymer-based composite materials, include at least two parts, a substrate (e.g., fibers, etc.) and a resin.

The composite materials include "Fiber-reinforced polymers" (FRP) including thermoplastic composites, short fiber thermoplastics, long fiber thermoplastics or long fiber-reinforced thermoplastics. There are numerous thermoset composites, but advanced systems usually incorporate aramid fiber and carbon fiber in an epoxy resin matrix. The composite materials also include carbon/carbon composite materials with carbon fibers and a silicon carbide matrix.

However, the present invention is not limited to these materials and other materials can be used to practice the invention.

In another embodiment, the outer surface 18 is constructed from Polyvinyl chloride (PVC) polyethylene and/or polypropylene. However, the present invention is not limited to these materials and other materials can be used to practice the invention.

Figure 4:
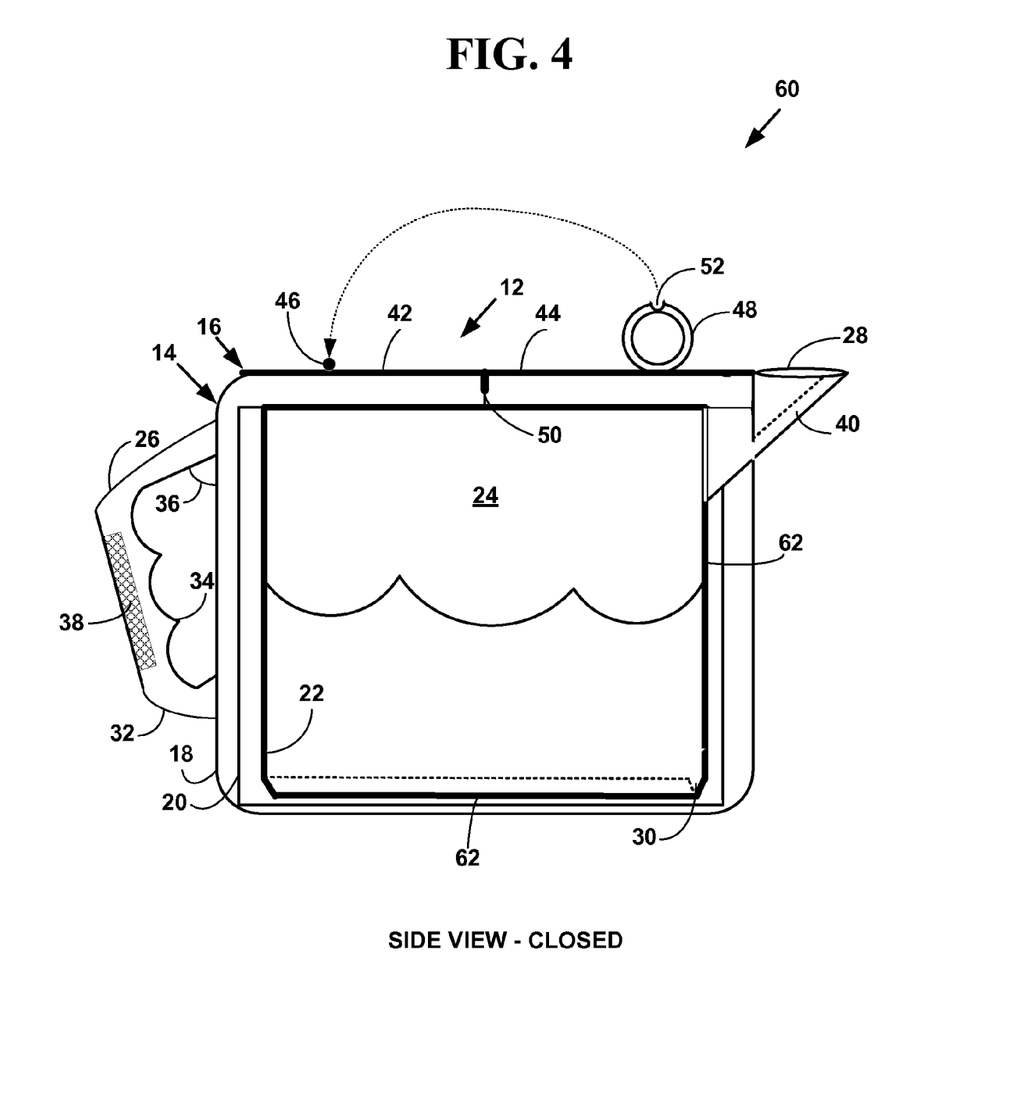
FIG. 4 is a block diagram illustrating a side view of the insulated disposable surgical fluid container device of FIG. 1 in a closed position with a layer of metalized polyester.

In one embodiment, the insulating component 20 separating the outer surface 20 from the inner surface 22 by the pre-determined distance is air. The air further reduces heat transfer from the inner surface 22 to the outer surface 18. In another embodiment, the insulating component 20 is a separate component with its own surfaces separated by a pre-determined distance and is filled with a fluid (e.g., water, alcohol etc.), gel (e.g., silicone, etc.) or another substance (e.g., another plastic, a polystyrene plastic, STYROFOAM® (STYROFOAM® is a type light, resilient polystyrene plastic), etc.). The pre-determined distance includes about 0.25 inches to about 1.0 inches. FIG. 4 illustrates insulating component 20 as a separate component.

In another embodiment, the insulating component 20 includes a separate sealed component in which all air has been roomed and is a "vacuum" component. A vacuum component is a component with a gaseous pressure much less than atmospheric pressure. The vacuum provides another layer of insulating material.

The insulating component 20 further prevents irrigation fluids in the fluid container portion 24 from losing heat and being affected by cooler temperatures in an operating room.

However, the present invention is not limited to these materials and distances and other distances materials can be used to practice the invention.

The inner surface 22 comprises a second wall of the container 12 and includes a fluid container portion 24 for holding a fluid (e.g., irrigation fluid, etc.). The inner surface 22 is thermally conductive material for spreading heat energy evenly over the inner surface and maintaining an isothermal temperature distribution on the inner surface, thereby maintaining an isothermal temperature of any fluid included in the fluid container portion 24. The inner surface 22 reflects heat back into fluids in the fluid container portion 24. The inner surface 22 helps to significantly reduce perioperative hypothermia caused by irrigating fluids at too cool a temperature used during a surgery.

In one embodiment, "thermal conductive plastics" are used for the inner surface 22 of the apparatus 12. However, the present invention is not limited to such an embodiment and more, fewer or other types materials for the inner surface 22 can be used to practice the invention.

The thermal conductivity of thermally conductive plastics about a 100 times the value of conventional plastics. The optimal level of thermal conductivity for any application depends on the heat input, size and the convection conditions. Values for thermal conductivity are typically measured in Watts per meter Kelvin (W/mK) for various materials.

At one most insulative end of the thermal conductivity range is foamed plastics like STYROFOAM®. Many plastics are actually foamed to enhanced their insulation characteristics because stagnant or trapped air is a very good thermal insulator.

Conventional plastics (e.g., PEI, etc.) are about an order or magnitude more conductive than air but are still considered thermal insulators. All plastics have a thermal conductivity near 0.2 W/mK regardless of their chemistry or typical additives. Glasses, like PYREX®, have a thermal conductivity of about 2 W/mK, which is about 10 times higher than plastics.

Thermally conductive plastic grades range in thermal conductivity from about 1 W/mK to as high as 100 W/mK. The majority of the grades are in the range 1 to 20 W/mK making them 5 to 100 times the conductivity of conventional plastics.

For comparison purposes, both stainless steel (at 15 W/mK) and the ceramic aluminum oxide (at about 25 W/mK) have thermal conductivities in this same range. Carbon steels have a thermal conductivity of about 50 W/mK. Pure aluminum has a conductivity greater than 200 W/mK but extrusion and casting alloys range from about 50 to 150 W/mK. Pure copper and silver have a thermal conductivity greater than 400 W/mK.

There is a heat transfer difference between a conventional and thermally conductive plastic. In a thermally conductive plastic heat energy is spread evenly throughout resulting in a more isothermal temperature distribution.

Heat transfer typically has three modes: conduction; convection; and radiation. Only the conduction mode is dependent on material conductivity. Heat often moves through a device faster than it can be removed from its surface. Thus, excess conductivity is often wasted. Thermally conductive plastics transfer heat like metals and ceramics. There is a non-linear relationship between heat transfer and thermal conductivity.

In one embodiment, thermally conductive elastomers are used. thermally conductive elastomers exhibit thermal conductivity in a flexible, compliant and soft touch material. Conventional elastomers are thermal insulators. The thermal conductivity of thermally conductive elastomers range from 1.0 W/mK to 15 W/mK. This exceptional level of thermal conductivity in an elastomer is about five to 75 times the value of conventional elastomer plastics. The optimal level of thermal conductivity for any application depends on the input (e.g., heat, etc.) size of the device and convection conditions.

Thermally conductive elastomers are thermoplastics that can be molded to 3-dimensional net shape objects 12 with conventional injection molding equipment. Other thermoplastic processing (e.g. extrusion, pultrusion, etc.) is also possible.

Thermally conductive elastomers are typically characterized by their hardness or Shore durometer. thermally conductive elastomers range in hardness from Shore A 40 (similar to a soft eraser) to Shore D 80 (similar to a bowling ball). thermally conductive elastomers are used to transfer heat and therefore must withstand the application temperature. thermally conductive elastomers have been used in applications up to 356° F. (180° C.). Thermally Conductive elastomers maintain the corrosion resistance of plastic and include the advantage of increased heat transfer rate.

The present invention is also not limited to the thermally conductive elastomers embodiment described and more, fewer or other types of plastics and/or thermally conductive elastomers can be used to practice the invention.

The whole apparatus 12 and/or separate components thereof may be injection molded, extruded, pultruded, pull-winded and/or manufactured and/or produced with other techniques. However, the present invention is not limited to such an embodiment and more, fewer or other types manufacturing techniques can be used to practice the invention.

"Extrusion" is a manufacturing process where a material is pushed through a die to create long objects of a fixed cross-section. Hollow sections are usually extruded by placing a pin or mandrel in the die. Extrusion may be continuous (e.g., producing indefinitely long material) or semi-continuous (e.g., repeatedly producing many shorter pieces). Some extruded materials are hot drawn and others may be cold drawn.

Feedstock for extrusion may be forced through the die by various methods: by an auger, which can be single or twin screw, powered by an electric motor; by a ram, driven by hydraulic pressure, oil pressure or in other specialized processes such as rollers inside a perforated drum for the production of many simultaneous streams of material.

"Pultrusion" is a continuous process for manufacture of materials with a constant cross-section. Reinforced fibers are pulled through a resin, possibly followed by a separate pre-forming system, and into a heated die, where the resin undergoes polymerization. Pultrusion is not limited to thermosetting polymers or polymides. More recently, pultrusion has been successfully used with thermoplastic matrices such either by powder impregnation of fibers or by surrounding it with sheet material of a thermoplastic/polymide matrix, which is then heated.

In one embodiment, components of the apparatus 12 are produced with an overwrapping transverse winding process that combines continuous filament winding with a pultrusion manufacturing process to produce a pultruded pullwound hollow cylindrical structure with the shape of hollow cylindrical structure that is used for components in apparatus 12.

The "pullwinding" process incorporates plural longitudinal reinforcement fibers with plural helical-wound (e.g., hoop, etc.) layers, providing maximum torsional properties and hoop strength. A self-contained inline winding unit is used with a pultrusion machine for feeding angled fibers between layers of unidirectional fibers before curing in a pultrusion die. The plural longitudinal re-enforcement fibers are used for axial and bending resistance while the plural helical-wound fibers are used for hoop tension and compression resistance. The pullwinding equipment is comprised of twin winding heads which revolve in opposite directions over a spindle. However, the present invention is not limited to such an embodiment and other embodiments can also be used to practice the invention.

In another embodiment, the apparatus 12 is constructed from surgical stainless steel, other metals, other plastics, ceramics, composite material and/or other materials, and/or combination thereof and is re-usable, autoclavable and sterilizable.

In one embodiment, the apparatus 12 is cast and includes zirconium dioxide ($ZrO_2$; also known as zirconia) and other types of ceramics. Ceramic containers 12 will not corrode in harsh surgical environments, are non-magnetic, and do not conduct electricity. Because of their resistance to strong acid and caustic substances. However, the present invention is not limited to such an embodiment and other embodiments can also be used to practice the invention.

Figure 5:
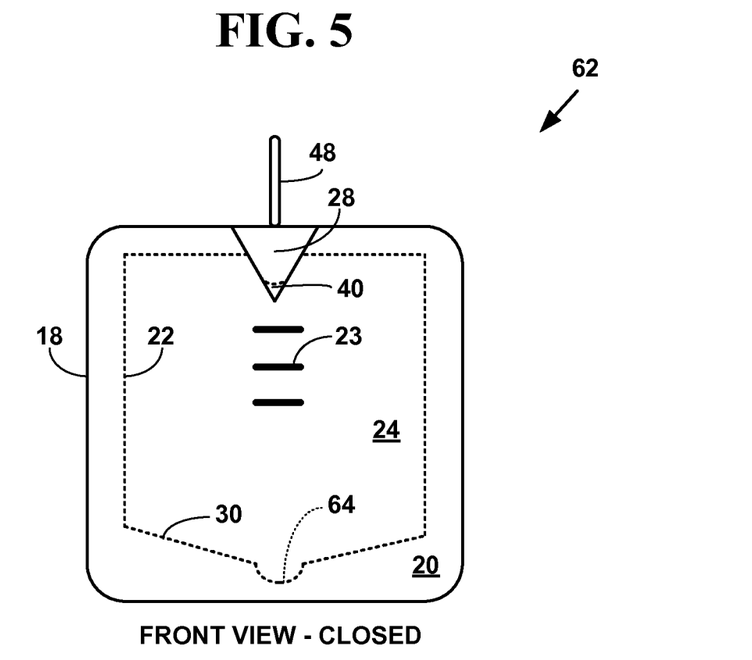
FIG. 5 is a block diagram illustrating a front view of an exemplary a keel shaped bottom portion.

The outer surface 18 and/or the inner surface 22 includes plural measurement marks 23 (only 3 of which are illustrated in FIG. 1 and FIG. 5) for accurately measuring fluids in the fluid container portion 24.

Returning to FIG. 1, the fluid container portion 24 includes a keel shaped bottom portion 30 for accurately dispending and pouring fluids from the container portion 24 into a wound during a surgery.

It has been determined experimentally that a keel shaped bottom portion 30 more accurately dispenses and pours fluids from a bottom of the fluid container portion 24.

The apparatus 12 is triangular in shape and is similar to a profile of a hull of a boat. One purpose of the keel shaped bottom portion 30 is to convert any sideways motion of the fluid generated by picking up, moving and/or tipping the apparatus 12 into a forward motion for accurate dispensing and pouring. The keel shaped bottom portion 30 functions in a similar manner as an actual keel on a boat does, by transferring motion forces applied to a fluid (e.g., water in the case of an actual boat) from one direction of motion (e.g., sideways, etc.) to another (e.g., forward, etc.) (See FIG. 6).

During a surgery, it is typically difficult to irrigate a wound because of the size of the wound, organs and issues exposed in the wound, other surgical instruments in the wound (e.g., retractors, suction devices, etc.). Irrigation fluids may be wasted or poured over tissues or organs that do not need irrigation as a result of inaccurate pouring and/or dispensing. It is also import to know how much irrigation solution is actually being used during a surgery. In addition, several ounces of the irrigation fluid may be wasted because pouring containers known in the art do not allow for easy removal of fluids from a bottom of a container when the fluid level is very low.

It is desirable to accurately dispense and pour all fluids from the fluid container portion 24 into the wound, especially when a fluid level in the container portion 24 is at a very low level. The keel shaped bottom portion 30 helps accomplish accurate pouring and dispensing of irrigation fluids, even when the when a fluid level in the container portion 24 is at a very low level, by transferring motion forces applied to a fluid from a sideways motion to a forward motion.

In one embodiment, the fluid container portion 24 holds about 640 fluid ounces (1000 mls or 1 liter) of solution. However, the present invention is not limited to this embodiment and larger, smaller and different size fluid container portions 24 may be used to practice the invention.

"Ergonomics" is a good 'fit' between a user, equipment and their environments. Ergonomics takes account of the user's capabilities and limitations in seeking to ensure that tasks, functions, information, safety and the environment suit each user. Ergonomic devices are produced to lower a number of or prevent injuries from using the device.

The ergonomic handle portion 26 includes a top surface 32 and a bottom surface 34. The ergonomic handle portion 26 is attached to the outer surface 18 at a pre-determined angle 36. The pre-determined angle is selected for optimal gripping comfort as well as optimal fluid pouring/dispensing capabilities. In one embodiment, the pre-determined angle is about ten to forty degrees. However, the present invention is not limited to such an embodiment and more, fewer or other types of handle attachment angles can be used to practice the invention.

The ergonomic handle portion 26 comprises a pre-determined pattern specifically sized and shaped for comfortable gripping by a human hand, the pre-determined angle allowing accurate pouring of fluids from the container portion into the wound during the surgery.

The ergonomic handle portion is designed for right or left-handed gripping and allows for easy pouring and dispensing control.

The top surface 32 includes a pre-determined pattern of protrusions 38 orientated along an axis of the top surface. The protrusions 38 help provide a surface that can be grasped with slippery surgical gloves covered with blood and/or other fluids.

In one embodiment, the protrusions are circular and/or oval and/or trapezoidal in shape. The protrusions prevent slipping during a surgery. The pre-determined pattern includes protrusions 38 of a same shape or combinations thereof of different shapes. However, the present invention is not limited to such an embodiment and more, fewer or other types of protrusions can be used to practice the invention.

In one embodiment, the top surface 32 includes a pre-determined cross-hatch pattern 38 (Illustrated in FIG. 1). The cross-hatch pattern 38 includes a pre-determined pattern of two or mores sets of intersecting parallel protrusions. One or more of the sets of intersecting parallel lines protrude up and away from the top surface. Cross-hatch patterns are often used on filing tools used in the construction industry. The protrusions on the cross-hatch pattern 36 provide a non-slip gripping surface on the handle 26.

In one embodiment, the cross hatch protrusions 38 are square, rectangular, circular and/or oval and/or trapezoidal in shape. The pre-determined pattern includes protrusions of a same shape or combinations thereof of different shapes. However, the present invention is not limited to such an embodiment and more, fewer or other types of protrusions can be used to practice the invention.

In another embodiment, surfaces of the handle 26 other than the bottom surface 34 of the ergonomic handle portion 18 includes the cross-hatching 38 pattern to provide additional gripping and non-slipping functionality. However, the present invention is not limited to such an embodiment and more, fewer or other types of gripping/non-slip surfaces can be used to practice the invention.

Returning to FIG. 1 the ergonomic handle portion 26 has a bottom surface 34 in a "wave" pattern specifically sized and shaped to be gripped by a human hand. The wave pattern 34 includes plural wave crests and wave depressions between the wave crests for engaging human fingers comfortably for gripping.

In another embodiment, the ergonomic handle portion 26 includes a twisted spiral shaped for engaging human fingers comfortably for gripping (Not illustrated in FIG. 1).

However, the present invention is not limited to such an embodiment and more, fewer or other types of gripping shapes and patterns can be used to practice the invention.

The pouring portion 28 also includes a keel shaped bottom portion 40 of the pouring portion 40 for accurately pouring fluids from the fluid container portion 24 into a wound during a surgery. It has been determined experimentally that a pouring portion 28 with a keel shaped bottom portion 40 also more accurately dispenses and pours fluids from the container portion 24 for the same reasons discussed above for 30.

The triangular shaped top portion 16 for covering the triangular shaped bottom portion 14 includes a first attached portion 42 and a second movable portion 44. The triangular shaped top portion 16 also includes an insulating material (e.g., PEI plastic, etc.) for reducing heat transfer from the fluids included in the fluid container portion 24 of the triangular shaped bottom portion 14 to the surrounding area.

In another embodiment, the first attached portion 42 comprises the entire triangular shaped top portion 16 is and removable/attachable.

The first attached portion 42 is attached to a top surface of the triangular shaped bottom portion 14 to cover a portion of the triangular shape bottom portion and prevent fluids from spilling out of the fluid container portion 24 and to prevent loss of heat energy from the fluids included in the fluid container portion 24 of the triangular shaped bottom portion 16. The first attached portion 42 includes a connection component 46 for connecting and attaching a cover handle portion 48 on the second moveable portion 44.

FIG. 4 illustrated the cover handle portion 48 as circular component. However, the present invention is not limited to such an embodiment and other shapes can be used to practice the invention.

The second moveable portion 44 is attached to the first attached portion 42 with a hinged component 50 including the cover handle portion for grasping the second moveable portion 44 to open and close triangular shaped top portion 16.

In one embodiment, the connection and attaching includes a snap connection means and/or a magnetic connection means and/or other connection means.

A "snap connection means" includes one or more bulbous protrusions 46 on the first attached portion 42 that engage one or more bulbous depressions 52 on the second moveable portion 44. In another embodiment, the snap connection means includes one or more bulbous protrusions on the second moveable portion 44 that engage one or more bulbous depressions first attached portion 42 (Not illustrated in FIG. 1).

A "magnetic connection means" includes small magnetic components placed on the connection component 46 for connecting and the cover handle portion 48. In such an embodiment only a small portion of the connection component 46 for connecting and the cover handle portion 48 include magnetic components since large magnetic fields may detrimental to other electronic equipment and metal instruments used during the surgery. For example, only portions of 46 and 52 are magnetic materials and/or may be coated with magnetic materials.

Various other types connection means can be used to keep the first attached component 42 and the second moveable component 44 connected. However, the present invention is not limited to the embodiments described and more, fewer and other equivalent connection means embodiments can also be used to practice the invention.

Figure 2:
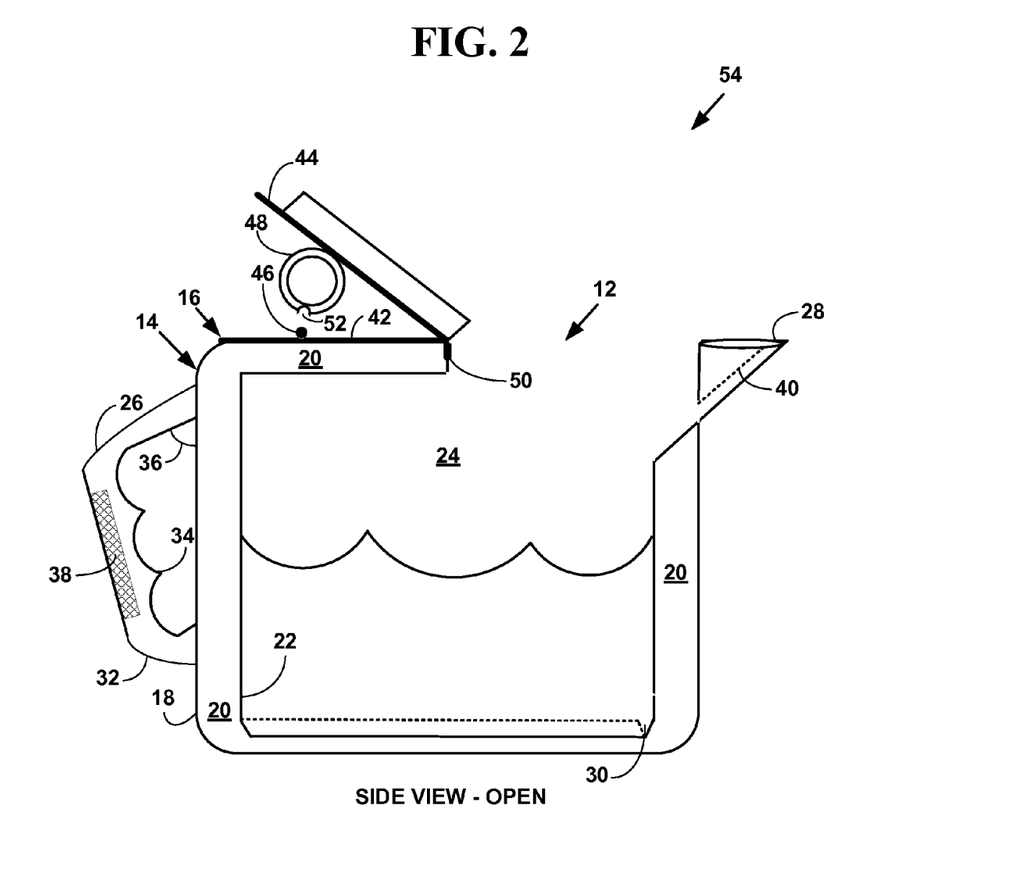
FIG. 2 is a block diagram illustrating a side of the insulated disposable surgical fluid container device of FIG. 1 with an open cover.

In another embodiment, the entire triangular shaped top component 16 is removable and re-attachable. In another embodiment, the second moveable portion 44 is long enough 53 to cover the pouring portion 28 as well to also prevent heat loss from irrigation fluid in the fluid container portion 24. However, the present invention is not limited to the embodiments described and more, fewer and other equivalent embodiments of the top cover can also be used to practice the invention FIG. 2 is a block diagram 54 illustrating a side view of the insulated disposable surgical fluid container 12 apparatus of FIG. 1 with the top cover 16 in an open position.

Figure 3:
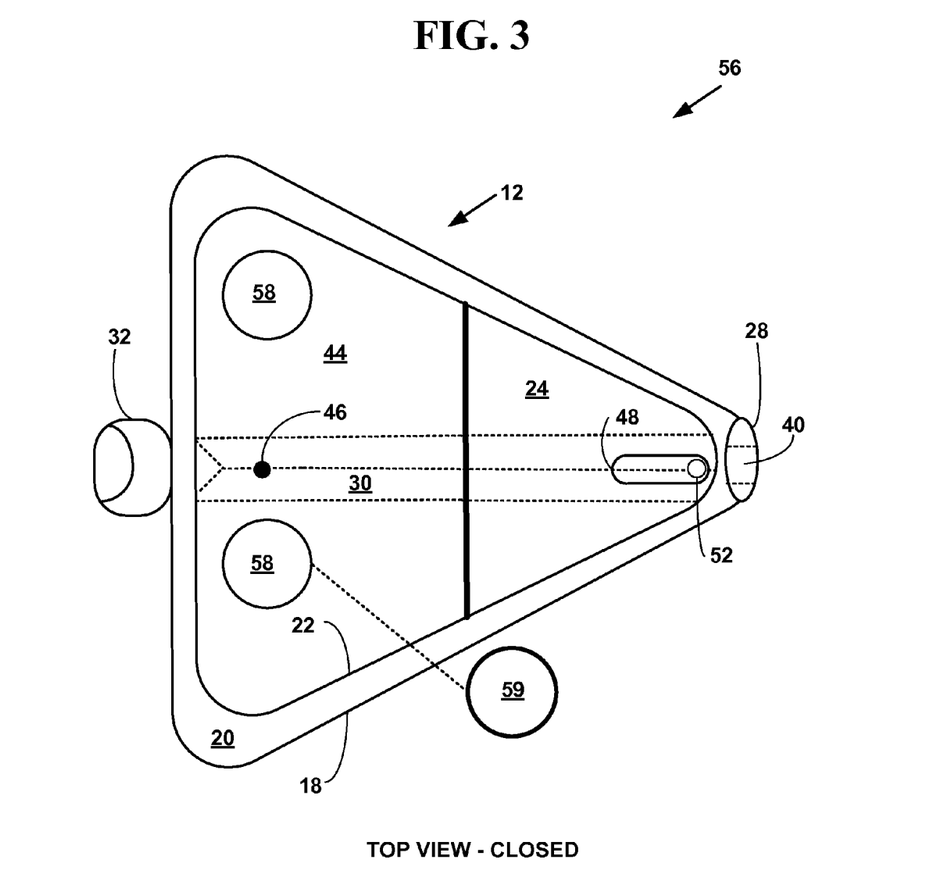
FIG. 3 is a block diagram illustrating a top view of the of the insulated disposable surgical fluid container device with a closed cover.

FIG. 3 is a block diagram 56 illustrating a top view of the of the insulated disposable surgical fluid container apparatus 12 in a closed position and its triangular shape.

In another embodiment, the triangular shaped top component 16 includes one or more openings 58 (two of which are illustrated in FIG. 3) in the triangular shaped top portion 16 for extracting fluids with an irrigation bulb syringe or other surgical device without having to open the apparatus 12. The one or more openings 58 helps prevent heat transfer/loss from the fluid since the cover of the apparatus 12 does not have to be re-opened once it is initially filled with irrigation fluid. The one or more openings 58 also include their own removable/re-attachable covers 59 to prevent heat loss from the fluids.

FIG. 4 is a block diagram 60 illustrating a side view of the insulated disposable surgical fluid container apparatus 12 of FIG. 1 in a closed position with a layer of metalized polyester 62.

In one embodiment, the outer surface 18 and/or insulating component 20 and/or inner surface 22 includes a layer of metalized polyester 62 (FIG. 4). The metalized polyester 62 is added to during manufacture of the apparatus 12.

The metallized polyester is very lightweight structure in which aluminum or other metals are deposited onto the surface of the polyester film (e.g., MYLAR® (Polyethylene Terephthalate)) in a thickness measured in angstroms (1 angstrom=about 1/1000th of a human hair). MYLAR® is a clear material made from polyester resin. In embodiment, the metalized polyester includes a thickness of about five to about 50 angstroms. However, the present invention is not limited to the embodiments described and more, fewer and other thicknesses and other embodiments can also be used to practice the invention.

In one embodiment, only the inner surface 22 includes a layer of metalized polyester 62 illustrated by the thick line in FIG. 4. The metalized polyesters further reflect heat energy back into the fluid container portion 24. This further helps further reduce radiation heat transfers from the fluid in the fluid container portion 24 either to the insulating component 20 or the outer surface 18 in a cool operating room during a surgery.

In another embodiment, only the insulating component 20 includes the metalized polyesters. In another embodiment, both the inner surface 22 and the insulating component 20 includes the metalized polyesters.

However, the present invention is not limited to the embodiments described and more, fewer and other embodiments can also be used to practice the invention.

Polyethylene terephthalate (sometimes written poly(ethylene terephthalate)), commonly abbreviated PET, PETE, or the obsolete PETP or PET-P, is a thermoplastic polymer resin of the polyester family and is used in synthetic fibers; beverage, food and other liquid containers, thermoforming applications and engineering resins often in combination with glass fiber. The term polyethylene terephthalate is often a source of confusion because PET, does not contain polyethylene at all.

FIG. 5 is a block diagram illustrating a front view 62 of the apparatus 12. FIG. 5 illustrates an exemplary keel shaped bottom portion 30 with a bulbous bow 64.

Figure 6:
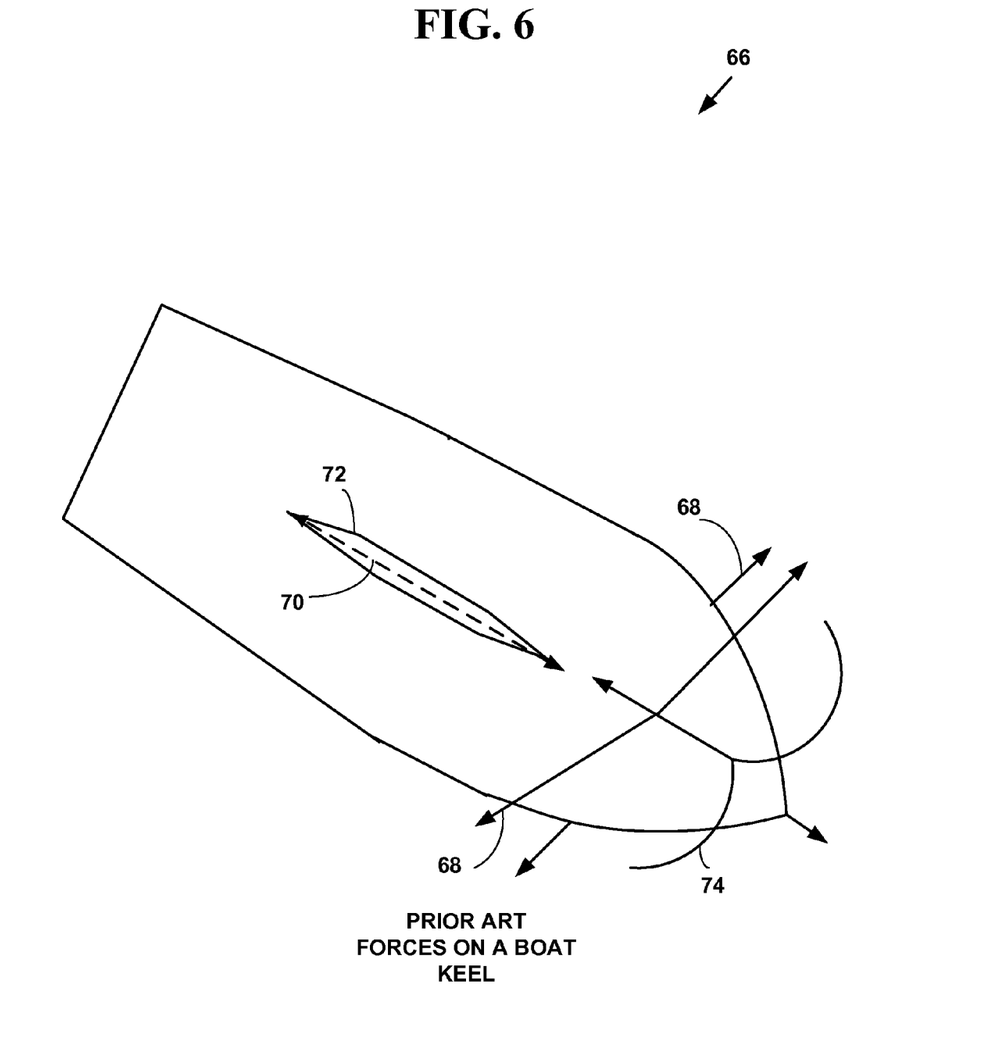
FIG. 6 is a block diagram illustrating transferring sideways forces to forward forces on a keel of an actual boat.

FIG. 6 is a block diagram 66 illustrating transferring sideways forces 68 to forward forces 70 on a keel 72 of an actual boat.

Returning to FIG. 5, the bulbous bow 64 modifies the way the fluid flows, changing its pressure distribution and cancels fluid waves created in the fluid by moving and pouring and reducing drag. The increases pouring efficiency and stability. The effect that pressure distribution has on a surface is known as the "form effect." The inner and outer shape of the apparatus 12 contributes to the form effect of the apparatus 12 and significantly aids fluid pouring and dispensing. However, the present invention is not limited to such an embodiment other keel shapes, with and without bulbous bows can also be used to practice the invention.

The apparatus 12 is triangular in shape and its fluid container 24 is similar to a profile shape of a hull of a boat. The keel shaped bottom portion 30 with the bulbous bow 64 further helps convert any sideways motion of the fluid generated by picking up, moving and/or tipping the apparatus 12 into a forward motion for accurate dispensing and pouring. The keel shaped bottom portion 30 with the bulbous bow 64 further functions in a similar manner as an actual keel 72 with a bulbous low on a boat does by transferring motion forces applied to a fluid (e.g., water 74 in the case of an actual boat, irrigation fluids in the case of the apparatus 12) from one direction of motion (e.g., sideways 68, etc.) to another (e.g., forward 70, etc.) (See. FIG. 6.)

FIG. 5 illustrates an exemplary keel shaped bottom portion 30 for the container portion 24. In one embodiment, the keel shaped bottom portion 40 on the pouring portion 28 is identical in shape with the bulbous bow 64 and is not illustrated for simplicity. In another embodiment, the keep shaped bottom portion 40 on the pouring portion 28 is a different shape and may or may not include the bulbous bow 64. However, it has been determined experimentally that use of two keel shape surfaces significantly improves pouring efficiency and/or stability and/or dispensing.

In one embodiment, apparatus 12 is an integral, one-time use, disposable component and is constructed from the materials just described. The apparatus 12 is constructed from an economical material (various plastics described above) and is intended to be a single-use, disposable apparatus. The apparatus 12 comes in a sterile package that is opened and used during a surgery. When the surgery is finished, the apparatus 12 is thrown away.

In another embodiment, the apparatus 12 is constructed from surgical stainless steel, other metals, plastic, ceramic composite material and/or other materials, and/or combination thereof and is re-usable, autoclavable and sterilizable.

In another embodiment, the inner surface 22 is a removable/insertable from the apparatus 12. In such an embodiment, the insulating component 20 is connected to the outer surface 18.

In another embodiment, the inner surface 22 is a removable/insertable one-time use, disposable component and is constructed from the materials described above. In this embodiment, the rest of the apparatus 12 is constructed from surgical stainless steel, other metals, plastic, ceramic composite material and/or other materials, and/or combination thereof and is re-usable, autoclavable and sterilizable.

There are other various combinations of components of the apparatus 12 that can be used to practice the invention using the materials described above to make the whole apparatus or portions thereof single-use and disposable and surgical stainless steel, other metals, plastic, ceramic composite material and/or other materials, and/or combination thereof can be used to make the whole apparatus 12 or portions thereof re-usable, autoclavable and sterilizable.

The apparatus 12 was described for use with surgery for humans. However, the apparatus 12 can also be used for surgery on animals (or plants) and is not limited to surgery for humans.

The apparatus 12 is a doubled walled container that keeps irrigation fluids used during a surgery at a proper temperature and avoids contributions to perioperative hypothermia during the surgery. Warmed fluids are keep warm in the apparatus 12 and are not cooled by temperatures in an operating room. A number of repetitive trips a circulating surgical nurse typically has to make to a fluid warmer (usually in an adjacent room) to keep getting irrigating solutions that are warm is significantly reduced and/or eliminated when apparatus 12 is used.

In addition, the apparatus 12 with its shape and keel shaped portions significantly improves the pouring and dispensing properties of apparatus 12 when used for storing moving, pouring and/or dispensing irrigation fluids during the surgery. This helps eliminate waste of irrigation fluids and helps more accurately flush unwanted materials from a wound of a patient during the surgery.

It should be understood that the architecture, processes, methods apparatus and devices described herein are not related or limited to any particular type of materials or design unless indicated otherwise. Various types of materials and designs may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams that describe any devices.

While various elements of the preferred embodiments have been specifically described as being implemented in specific designs and materials, in other embodiments other designs and materials may alternatively be used, and vice-versa.

The claims should not be read as limited to the described order or elements unless stated to that effect. In addition, use of the term "means" in any claim is intended to invoke 35 U.S.C. §112, paragraph 6, and any claim without the word "means" is not so intended.

Therefore, all embodiments that come within the scope and spirit of the following claims and equivalents thereto are claimed as the invention.

I claim:

1. An insulated disposable surgical fluid container apparatus, comprising in combination:
    a triangular shaped bottom portion including an outer surface, an insulating component between the outer surface and an inner surface separating the outer surface from the inner surface by a pre-determined distance, an ergonomic handle portion, and a pouring portion;
    the outer surface including an insulating material for reducing heat transfer from the outer surface to a surrounding area,
    the insulating component separating the outer surface from the inner surface by the pre-determined distance for reducing heat transfer from the inner surface to the outer surface,
    the inner surface comprising a fluid container portion for holding a fluid including an thermally conductive material for spreading heat energy evenly over the inner surface and maintaining an isothermal temperature distribution on the inner surface, thereby maintaining an isothermal temperature of any fluid included in the fluid container portion,
    the fluid container portion including an inverted triangular shaped bottom portion along a longitudinal centerline and extending into a bulbous shaped longitudinal groove in the bottom portion for accurately dispending and pouring fluids from the fluid container portion into a wound during a surgery,
    the ergonomic handle portion attaching to the outer surface at a pre-determined angle comprising a pre-determined pattern specifically sized and shaped for comfortable gripping by a human hand, the pre-determined angle allowing accurate pouring of fluids from the fluid container portion into the wound during the surgery, and
    the pouring portion including another inverted triangular shaped bottom portion along a longitudinal centerline and extending into a bulbous shaped longitudinal groove in the pouring portion for accurately pouring fluids from the fluid container portion and the pouring portion into a wound during a surgery; and
    a triangular shaped top portion for covering the triangular shaped bottom portion including a first attached portion and a second movable portion;
    the triangular shaped top portion including an insulating material for reducing heat transfer from the fluids included in the fluid container portion of the triangular shaped bottom portion to the surrounding area,
    the first attached portion attached to a top surface of the triangular shaped bottom portion to cover a portion of the triangular shape bottom portion and prevent fluids from spilling out of the fluid container portion and to prevent loss of heat energy from the fluids included in the fluid container portion of the triangular shaped bottom portion including a connection portion for connecting and attaching a cover handle portion on the second moveable portion, and
    a second moveable portion attached to the first attached portion with a hinged component including the cover handle portion for grasping the second moveable portion to open and close triangular shaped top portion.

2. The insulated disposable surgical fluid container apparatus of claim 1 wherein the outer surface includes polyetherimide, polyimide, other thermosetting polyimides or composite materials.

3. The insulated disposable surgical fluid container apparatus of claim 1 wherein the inner surface includes thermally conductive elastomers.

4. The insulated disposable surgical fluid container apparatus of claim 1 wherein the inner surface further includes one more layers of metalized polyester for further reflecting heat energy from the inner surface back into the fluid included in the fluid container portion.

5. The insulated disposable surgical fluid container apparatus of claim 1 wherein the inner surface is a removable component.

6. The insulated disposable surgical fluid container apparatus of claim 1 wherein the ergonomic handle includes a wave pattern shape or a twisted spiral shape for comfortably engaging human fingers.

7. The disposable surgical fluid container apparatus of claim 1 wherein the cover handle portion of the second moveable portion is connected to the connection component on the first fixed portion with a snap connection means or a magnetic connection means.

8. The disposable surgical fluid container apparatus of claim 1 wherein apparatus is an integral, single-use, disposable apparatus.

9. The disposable surgical fluid container apparatus of claim 1 wherein the triangular shaped top component includes one or more openings for extracting fluids with an irrigation bulb syringe or other surgical device without having to open the triangular shaped top component.

10. The disposable surgical fluid container apparatus of claim 1 wherein the insulating component separating the outer surface from the inner surface includes air, a fluid, a gel, or plastic material or includes a vacuum component.

11. An insulated surgical fluid container apparatus, comprising in combination:
    a triangular shaped bottom portion including an outer surface, an insulating component between the outer surface and a removable inner surface separating the outer surface from the removable inner surface by a pre-determined distance, an ergonomic handle portion, and a pouring portion,
    the outer surface including an insulating material for reducing heat transfer from the outer surface to a surrounding area,
    the insulating component separating the outer surface from the removable inner surface by the pre-determined distance for reducing heat transfer from the removable inner surface to the outer surface, the removable inner surface comprising a fluid container portion for holding a fluid including an thermally conductive material for spreading heat energy evenly over the removable inner surface and maintaining an isothermal temperature distribution on the removable inner surface, thereby maintaining an isothermal temperature of any fluid included in the fluid container portion, the fluid container portion including an inverted triangular shaped bottom portion along a longitudinal centerline and extending into a bulbous shaped longitudinal groove in the bottom portion with a bulbous shaped portion for accurately dispensing and pouring fluids from the fluid container portion into a wound during a surgery, the ergonomic handle portion attaching to the outer surface at a pre-determined angle comprising a pre-determined pattern specifically sized and shaped for comfortable gripping by a human hand, the pre-determined angle allowing accurate pouring of fluids from the fluid container portion into the wound during the surgery, and the pouring portion including another inverted triangular shaped bottom portion along a longitudinal centerline and extending into a bulbous shaped longitudinal groove in the pouring portion for accurately pouring fluids from the fluid container portion and the pouring portion into a wound during a surgery;

a triangular shaped top portion for covering the triangular shaped bottom portion including a first attached portion and a second movable portion;

the triangular shaped top portion including an insulating material for reducing heat transfer from the fluids included in the fluid container portion of the triangular shaped bottom portion to the surrounding area, the first attached portion attached to a top surface of the triangular shaped bottom portion to cover a portion of the triangular shape bottom portion and prevent fluids from spilling out of the fluid container portion and to prevent loss of heat energy from the fluids included in the fluid container portion of the triangular shaped bottom portion including a connection portion for connecting and attaching a cover handle portion on the second moveable portion, and a second moveable portion attached to the first attached portion with a hinged component including the cover handle portion for grasping the second moveable portion to open and close triangular shaped top portion.

12. The surgical fluid container apparatus of claim 11 wherein the apparatus is constructed from surgical stainless steel, other metals, plastics, ceramics, composite materials or combinations thereof and is a re-usable, autoclavable and sterilizable apparatus.

13. The insulated surgical fluid container apparatus of claim 11 wherein the outer surface includes polyetherimide, polyimide, other thermosetting polyimides or composite materials.

14. The insulated surgical fluid container apparatus of claim 11 wherein the inner surface includes thermally conductive elastomers.

15. The disposable surgical fluid container apparatus of claim 11 wherein the inner surface further includes one more layers of metalized polyester for further reflecting heat energy from the inner surface back into the fluid included in the fluid container portion.

* * * * *